(12) United States Patent
Miersch

(10) Patent No.: US 12,007,036 B2
(45) Date of Patent: Jun. 11, 2024

(54) STOPCOCK, HOUSING OF A STOPCOCK, AND METHOD FOR PRODUCING A HOUSING OF A STOPCOCK

(71) Applicant: OLYMPUS WINTER & IBE GMBH, Hamburg (DE)

(72) Inventor: Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 17/688,411

(22) Filed: Mar. 7, 2022

(65) Prior Publication Data

US 2022/0282799 A1 Sep. 8, 2022

(30) Foreign Application Priority Data

Mar. 5, 2021 (DE) .................... 10 2021 105 353.6

(51) Int. Cl.
*F16K 27/06* (2006.01)
*A61M 39/22* (2006.01)
(Continued)

(52) U.S. Cl.
CPC ........... *F16K 27/062* (2013.01); *A61M 39/22* (2013.01); *A61B 1/015* (2013.01);
(Continued)

(58) Field of Classification Search
CPC ...... F16K 27/062; F16K 5/0414; F16K 5/163; F16K 5/165; F16K 5/0292; F16K 5/167; F16K 11/08–0856; A61M 2039/229; A61M 39/22; A61B 1/015; Y10T 137/86823; Y10T 137/4259; Y10T 137/86871; Y10S 251/904
(Continued)

(56) References Cited

U.S. PATENT DOCUMENTS 3,012,752 A * 12/1961 Buck ..................... F16K 5/0414
D24/129
3,678,960 A * 7/1972 Leibinsohn ......... A61M 39/223
251/309
(Continued)

FOREIGN PATENT DOCUMENTS

DE 20201 0004 098 U1 8/2011
DE 10 2017 129 033 A1 6/2019
JP S63275314 A 11/1988

*Primary Examiner* — Craig J Price
(74) *Attorney, Agent, or Firm* — Oliff PLC

(57) ABSTRACT

A medical endoscope is an instrument having an elongate, tubular shaft. The instrument is commonly provided with a flushing device. The flushing liquid can be guided through corresponding separate liquid channels. In order to be able to control the flow of the liquid, the liquid channels have a stopcock. The stopcocks here are of complex construction, and for this reason both the production thereof and the cleaning thereof are complicated. The invention includes a stopcock and also a housing and a method for producing the housing, by way of which the production and the cleaning of the housing are simplified. This is achieved in that a housing and at least one spring element for form-fitting fixing of a plug in a position in the interior space of the housing are manufactured integrally from a single part, that is to say in one part.

12 Claims, 2 Drawing Sheets

(51) Int. Cl.
*A61B 1/015* (2006.01)
*F16K 11/083* (2006.01)

(52) U.S. Cl.
CPC .... *A61M 2039/229* (2013.01); *F16K 11/0836* (2013.01); *Y10S 251/904* (2013.01); *Y10T 137/86823* (2015.04); *Y10T 137/86871* (2015.04)

(58) Field of Classification Search
USPC ...... 251/309–312, 315.11, 315.12, 181, 182, 251/111, 97, 904; 604/248; 137/625.47
See application file for complete search history.

(56) References Cited

U.S. PATENT DOCUMENTS

| | | | | |
|---|---|---|---|---|
| 3,779,513 | A * | 12/1973 | Levine | F16K 5/0292 251/309 |
| 3,788,599 | A * | 1/1974 | Cloyd | F16K 5/025 251/181 |
| 4,014,512 | A * | 3/1977 | Cheever | F16K 5/165 251/181 |
| 4,207,923 | A * | 6/1980 | Giurtino | F16K 11/0853 251/181 |
| 4,314,586 | A * | 2/1982 | Folkman | F16K 11/0853 251/368 |
| 4,807,666 | A * | 2/1989 | Morse | F16K 11/0853 251/366 |
| 4,929,468 | A * | 5/1990 | Mullendore | C23C 16/16 427/598 |
| 4,958,802 | A * | 9/1990 | Underwood | F16K 27/065 251/310 |
| 5,234,193 | A * | 8/1993 | Neal, Jr. | F16K 27/065 251/317 |
| 5,341,833 | A * | 8/1994 | Davis | B60C 29/06 137/232 |
| 5,832,959 | A * | 11/1998 | Szymczakowski | A61M 39/223 251/297 |
| 6,012,702 | A * | 1/2000 | Heimberger | F16K 27/062 137/240 |
| 6,536,742 | B2 | 3/2003 | Lotz et al. | |
| 6,652,489 | B2 * | 11/2003 | Trocki | A61M 5/31576 600/432 |
| 7,012,752 | B2 * | 3/2006 | Choi | G01J 3/26 359/578 |
| 7,152,845 | B2 * | 12/2006 | Carrez | F16K 35/04 251/297 |
| 7,326,188 | B1 * | 2/2008 | Russell | A61M 39/24 604/248 |
| 7,744,573 | B2 * | 6/2010 | Gordon | A61B 5/150824 604/32 |
| 7,771,383 | B2 * | 8/2010 | Truitt | A61M 39/26 604/32 |
| 7,887,584 | B2 * | 2/2011 | Richter | A61L 17/145 623/2.42 |
| 7,984,730 | B2 * | 7/2011 | Ziv | F16K 27/065 137/239 |
| 9,089,681 | B2 * | 7/2015 | Ueda | A61M 39/22 |
| 9,347,208 | B2 * | 5/2016 | Quinn | E03C 1/0412 |
| 9,995,405 | B2 * | 6/2018 | Duncan | F16K 11/0853 |
| 10,969,022 | B2 * | 4/2021 | Miersch | F16K 5/165 |
| 11,007,361 | B2 * | 5/2021 | Murphy-Chutorian | A61M 1/3649 |
| 11,306,832 | B2 * | 4/2022 | Mermelshtein | A61M 5/16877 |
| 2017/0258991 | A1 | 9/2017 | Tornblom | |

* cited by examiner

STOPCOCK, HOUSING OF A STOPCOCK, AND METHOD FOR PRODUCING A HOUSING OF A STOPCOCK

The invention relates to a housing of a stopcock for producing and breaking a fluidic connection between at least two connection parts. The invention furthermore relates to a stopcock for a hand-held medical instrument. Finally, the invention also relates to a method for producing a housing of a stopcock.

Medical endoscopes are instruments having an elongate, tubular, flexible or rigid shaft and having an optical unit, which are used for optical, minimally invasive examination of interior spaces of the human body and for minimally invasive surgery. Passage instruments, such as stone-collecting baskets, instruments for electrosurgical resection or forceps, can be guided to the surgical site through the shaft section of the endoscopes. In order to flush away local bleeding which occurs during surgery and to protect tissue for example from heat damage due to a high-frequency electrosurgical application, the endoscopes are commonly provided with a flushing device which permanently flushes around the tissue which is situated in front of the distal shaft end. The flushing liquid can be guided through an inner tube or through an outer tube of the instrument by way of corresponding separate liquid channels. In order to be able to control the inflow and outflow of the liquid, the liquid channels generally have a stopcock in their proximal end region. Furthermore, it is also possible for work channels for passage of instruments to be blocked off by way of stopcocks. Corresponding stopcocks are described for example in DE 10 2014 002 158 B4 and DE 10 2016 011 184 A1.

The stopcocks commonly consist of a housing and a plug which can be rotated therein, the walls of which sealingly adjoin one another. In order to produce a fluid-tight or form-fitting connection between the housing and the plug, it is very important that the plug can be fixed in a corresponding closed position, and also in an open position. In the case of known stopcocks, a spring element is used for this purpose. Said spring element is generally connected to the housing during assembly and, in relation to the plug, exerts a mechanical stress which results in the form-fitting fixing of the plug.

Known stopcocks or the housings of these stopcocks consist of steel. The spring element is produced from a spring steel. These two parts of the stopcock, that is to say the housing and the at least one spring element, are connected to one another. Equally, it is also known for the spring element to be assigned to the plug. This two-part or multi-part embodiment of the housing and the element is disadvantageous in particular for the production of the stopcock, since this multi-part design necessitates additional processes, specifically for example the latching-on of a cap or the re-melting of a holding pin for fixing the element. This additional process is not only time-consuming but also entails the risk of incorrect assembly or a material defect of at least one of the components. Furthermore, a multi-part component is always disadvantageous with regard to cleaning capability. The multi-part design gives rise to gaps and cracks between the individual parts. These entail the risk of germs accumulating there. Said gaps and cracks can be reached only with difficulty using the common cleaning methods, and so an increased cleaning outlay is necessary here.

Proceeding from this, the problem addressed by the present invention is that of providing a stopcock and also a housing of a stopcock and a method for producing the housing, by way of which the stated problems are eliminated.

A solution to this problem is achieved based on the features discussed below. Accordingly, it is provided that the housing of the stopcock for producing and breaking a fluidic connection between at least two connection parts and the at least one spring element for form-fitting fixing of a plug in a position in the interior space of the housing are manufactured integrally from a single part, that is to say in one part. As a result of this one-part design, additional manufacturing steps are dispensed with, which results in both a time saving and lower production costs. Furthermore, the risk of incorrect assembly or a defective material can be reduced. Altogether, the production costs can thus be reduced by this one-part solution. Additionally, a one-part housing which integrally comprises the at least one spring element does not have any difficult-to-access gaps or cracks which are unreachable using the common cleaning processes. Rather, the housing described here with the integral spring element can be cleaned particularly easily and also efficiently and thoroughly. Due to the reduction in the cleaning outlay, it is also the case that the costs associated with the use of the stopcock are reduced over the long term.

Preferably, the invention provides that the housing has at least two, three, four, five, six or more spring elements. It may be advantageous for the plug to be fixed in the housing in various ways according to type and application area. Also, the type and the configuration or the shape of the housing permit different numbers of spring elements. In this regard, it may for example for a cylindrical housing be advantageous for the housing to have three or four spring elements. Ultimately, the type and the number of the spring elements allow the fixing or a spring strength of the housing for the plug to be set.

A particularly advantageous exemplary embodiment of the invention may provide that the housing of the stopcock is produced, in particular injection-moulded, from an amorphous metal. Amorphous metals have material properties which are particularly highly suitable both for use for the manufacture of the housing described here and for the spring elements. In this regard, amorphous metals have a higher yield strength and hardness than steels and at the same time an elasticity which has hitherto been attainable only by plastics. Furthermore, amorphous metals exhibit an extraordinary resistance to corrosion, which surpasses that of high-grade steels. These properties of amorphous metals enable use in extreme environments and in the field of medical technology, in particular due to proven biocompatibility.

In particular, the invention may furthermore provide that the at least one spring element is oriented parallel, perpendicularly or transversely to a longitudinal axis which extends perpendicularly through the housing, or that the at least one spring element includes an angle with the longitudinal axis. The orientation of the spring elements that is claimed here makes it possible for particularly efficient spring-preloaded fixing of the plug in the interior space of the housing to be achieved. In particular the axial orientation is particularly efficient and simple to achieve.

A further exemplary embodiment of the invention may provide that the at least one spring element is formed from a housing wall of the housing, wherein the at least one spring element, preferably as an extension of the housing wall, is formed parallel to the longitudinal axis and forms a spring preload perpendicular to the longitudinal axis. By virtue of the one-part design of the housing and the at least one spring element, it is expedient for the spring element to be integrated directly into the form of the housing wall. In this way, the sealing surfaces between the housing and the plug merge directly into the spring elements. This permits a particularly simple form, which is thus simple to produce, on the one hand, and such a simple form can be cleaned particularly thoroughly and reliably, on the other hand.

Preferably, it is furthermore provided that a thickness of the at least one spring element differs from, that is to say is larger than or smaller than, a wall thickness of the housing wall. Whereas the wall thickness of the housing has to be of relatively thick form, in order to ensure sufficient stability, the thickness of the at least one spring element may be reduced, so as, on the one hand, to save material and, on the other hand, to achieve a corresponding spring action. Equally, it is also conceivable for the thickness of the spring elements to vary parallel to the longitudinal axis, so that lower sections of the spring elements have a smaller or larger thickness than upper sections. This variation of the spring thickness makes it possible to produce the optimum spring action for any exemplary embodiment of a stopcock.

Furthermore, it is conceivable that at least two spring elements are formed in a tab-like manner from the housing wall, and recesses are formed in the housing wall between the two tab-like spring elements. By virtue of this tab-like form and by virtue of the recesses, the spring elements acquire a particularly advantageous and reversible property or spring property. The spring load of the spring elements can be varied in particular by way of the dimensioning of the width of the tabs and of the recesses. If, for example, only a small spring force is desired, in order that the plug can be removed from the housing for example without action of large forces, the width of the tabs may be reduced. Equally, a large spring force can be generated by way of a large tab width.

A further embodiment of the invention may provide that at least three tab-like spring elements are formed from the housing wall, between which spring elements a recess is formed in the housing wall in each case. For a large number of housing shapes, whether they are rectangular or cylindrical, it is expedient to have three spring elements since this constitutes a balance between flexibility and strong spring action. Equally, it is however also conceivable for four, five, six or more tab-like spring elements to be formed from the housing wall.

A further exemplary embodiment of the invention may provide that the recesses between two spring elements are of wedge-like form, wherein openings of the wedge-like recesses are oriented towards a bottom side of the housing. The spring behaviour of the spring elements can be varied by way of this specific embodiment of the recesses too.

It is furthermore conceivable that the at least one spring element has at least one preferably web-like latching means which serves for form-fitting fixing of the plug. Known plugs have in their outer wall notches in which corresponding webs or other latching elements can engage in order to fix or to guide the movement of the plug in the housing. By way of said latching means, it can be ensured that the resilient action also acts on the plug and the plug is fixed in the sealing position. Equally, the latching means are formed in such a way that the latching connection between the spring elements and the plug can be released by way of a corresponding action of force.

A further particularly advantageous exemplary embodiment of the invention provides that the interior space of the housing is of conical form, wherein the housing wall converges towards a bottom side of the housing. The at least one spring element follows the conical shape in this case or is formed in a cylindrical manner relative to the longitudinal axis. In this case, the housing wall can, along the longitudinal axis, transition into the cylindrical shape, which is associated with the spring elements, from the conical shape towards the bottom end of the housing. The funnel-like cross section of the housing that is thus formed forms a particularly advantageous sealing surface with the plug, on the one hand, and forms the spring elements oriented parallel to the longitudinal axis, on the other hand. This orientation makes it possible to achieve a particularly efficient spring performance and, at the same time, the required sealing action of the stopcock.

A further solution to the problem stated at the outset is described by a stopcock for producing and breaking a fluidic connection between at least two connection parts is provided, wherein said stopcock has a housing. Said stopcock may be assigned for example to a medical instrument, such as for example an endoscope.

A method for solving the stated problem is described by a housing of the stopcock and at least one spring element are produced in one part. This one-part production results in both the manufacturing and the cleaning of the housing being simplified. The simplification of the production allows considerable costs to be saved and risks which can arise during the assembly of the housing to be reduced. The simpler form of a one-part housing furthermore makes provision for fewer gaps and cracks in which impurities which are removable only with difficulty or not at all or only with increased effort can accumulate.

One possible exemplary embodiment of the invention is illustrated schematically in the drawings. In the drawings.

Figure 1:
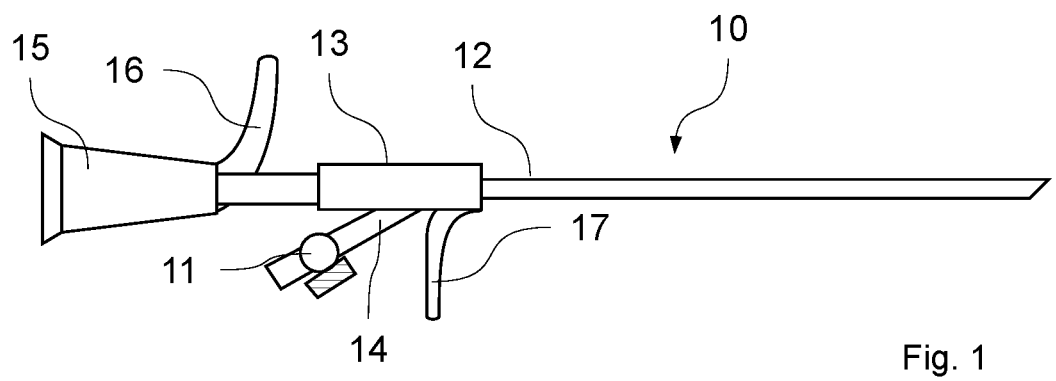
FIG. 1 shows a schematic side view of an endoscope with a stopcock.

FIG. 1 highly schematically illustrates an endoscope 10. Said endoscope 10 has a stopcock 11. A liquid channel (not visible here) runs within a shaft part 12 of the endoscope 10 and passes, angled, by way of a main body 13, to an inlet connector 14. The stopcock 11 is arranged on the inlet connector 14 for the purpose of regulating the liquid flow through the liquid channel. A pump for feeding liquid into the liquid channel, for example, may be connected to the inlet connector 14.

The side view illustrated here shows the medical endoscope 10 in the orientation in which it is normally used during an operation. The endoscope 10 has at its proximal end an eyepiece 15 for observation of the operation area. In order for the operator to be able to securely hold the endoscope 10 during the operation, two grip pieces 16, 17 are fastened to the endoscope 10. The grip pieces 16, 17 are normally formed ergonomically in such a way that the operator can hold the endoscope 10 in one hand with the aid of the grip pieces 16, 17. The operator correspondingly has the other hand free in order, for example, to introduce passage instruments into a work channel of the instrument and to operate them.

Figure 2:
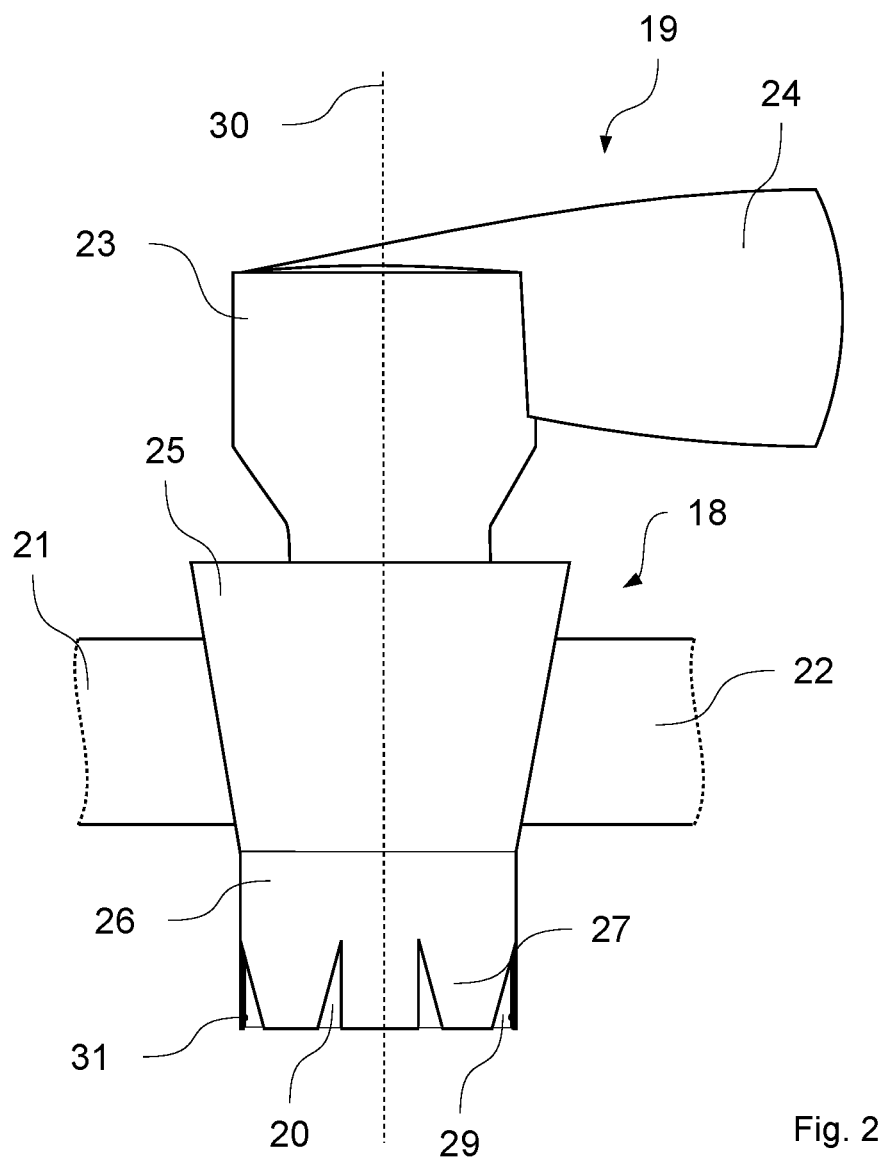
FIG. 2 shows a schematic side view of a stopcock according to the invention.

FIG. 2 highly schematically illustrates one possible exemplary embodiment of the stopcock 11 according to the invention. Said stopcock 11 has a housing 18 and a plug 19, the cone part 20 (not visible here) of which plug is received in the housing 18. The housing 18 has two connection parts 21, 22, by way of which it can be coupled to the inlet connector 14 of the endoscope 10. It is also possible for connecting parts, such as further valves or the like, to be assigned to said two connection parts 21, 22.

As can be seen in FIG. 2, the plug 19 has a grip 23 which comprises a grip part 24. The grip part 24 may, for this purpose, be ergonomically formed, so as to facilitate holding and movement by the user.

Figure 3:
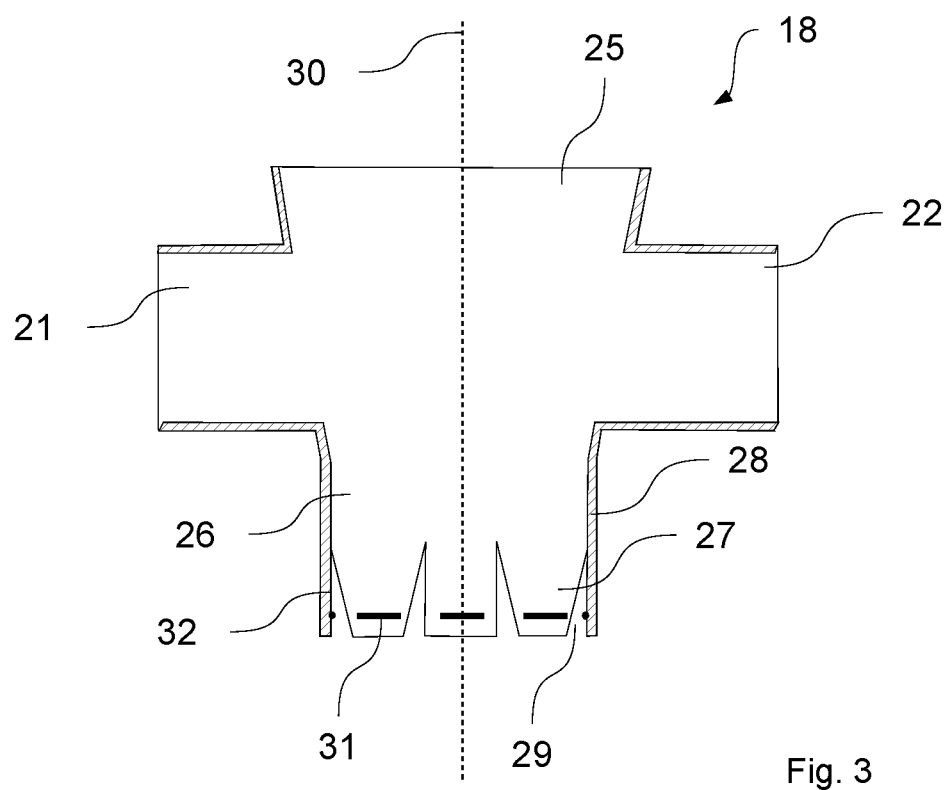
FIG. 3 shows a schematic side view of a housing according to the invention.

According to the invention, the exemplary embodiment illustrated in FIGS. 2 and 3 of the housing 18 is formed in one part. As can be seen in FIG. 2, the housing 18 may be subdivided into two sections, specifically into an upper section 25 and into a lower section 26. The upper section 25 has a conical cross section, and the lower section 26 has a cylindrical cross section. As illustrated in the figures, these two sections 25 and 26 merge into one another in a transition-free manner. It should however be expressly pointed out that this represents merely one of many possible embodiments of the housing 18. Equally, it is also conceivable for the entire housing 18 to be of conical form or for there to be a shoulder between the upper section 25 and the lower section 26. In this case, the form-fitting connection of the plug 19 and the housing 18 exists only in the upper section 25, while the fixing of the plug 19 in the housing 18 is realized by way of the lower section 26 or the spring elements 27.

In the exemplary embodiment illustrated here, multiple spring elements 27 are assigned to the lower section 26 of the housing 18. Said multiple spring elements 27 are formed integrally by the wall 28 of the housing 18. In this case, the spring elements 27, which are of tab-like form here, are separated from one another by recesses 29. Said recesses may, as illustrated in FIGS. 2 and 3, be of triangular form. Equally, it is however also conceivable for the recesses 29 to be of rectangular or round form. However, it is also conceivable for said recesses 29 to be different from one another, so that also the spring elements 27 are not identical in terms of their shape. By way of said recesses 29, which ultimately form the spring elements 27, the spring elements 27 acquire their resilient action. Specifically, the spring elements 27 can be moved transversely or perpendicularly to a longitudinal axis 30 of the housing 19, wherein, by virtue of the reversibility of the material, the spring elements 27 always revert back into their initial position.

The spring force or the preload can be regulated by way of the length of the tab-like spring elements 27 parallel to the longitudinal axis 30 and by way of a width of the spring elements 27 transverse to the longitudinal axis 30. It is conceivable for the housing 18 to have merely two spring elements 27 or a multiplicity, which are formed in the wall 28 of the housing 18.

The sectional illustration of the housing 18 in FIG. 3 shows that a wall thickness of the upper section 25 and a wall thickness of the lower section 26, or a wall thickness of the housing 18 and a wall thickness of the spring elements 27, are equal. Equally, it is however also provided according to the invention that the wall thickness varies between the upper section 25 and the lower section 26. Furthermore, it is also conceivable that the wall thickness of the lower section 26 varies, and decreases in the downward direction, too. In this way, it is possible in particular for the resilient action of the spring elements 27 to be varied further.

The spring elements illustrated in FIG. 3 have web-like latching means 31 towards the open end of the housing 18. Said latching means 31 are situated on an inner side 32 of the wall 28 and are oriented transversely to the longitudinal axis 30. Equally, it is however also conceivable for said latching means 31 to be oriented so as to be slightly inclined in relation to the longitudinal axis 30. Said latching means engage into corresponding recesses in the cone part 20 of the plug 19. This engagement of the multiple latching means 31 into the recesses of the plug 19 results in the plug 19 being fixed in the interior space of the housing 18. This first connection thus ensures that the plug 19 is connected in a form-fitting or fluid-tight manner to the housing 18. By rotation of the grip 23, the fluidic connection between the connection parts 21 and 22 can be produced or broken. For a more detailed description of the configuration of the plug 19, reference is made to the relevant prior art.

An essential feature of the invention is that the housing 18 and the spring elements 27 are produced in one part from an amorphous metal. By virtue of the specific material properties, an amorphous metal is particularly highly suitable for manufacture of the housing 18 or of the upper section 25 and for manufacture of the spring elements 27. At the same time, an amorphous metal exhibits a high degree of stability or strength and a high degree of flexibility. Thus, an amorphous metal combines the properties of high-grade steel and plastic. Whereas provision of sufficient stability is of great importance for the upper section 25, the material for the above-described fixed connection between the housing 18 and the plug 19 has to be sufficiently flexible. An amorphous metal satisfies precisely these requirements.

Furthermore, the housing 18 described here can be produced particularly easily and inexpensively. This is because, by virtue of the selection of an amorphous metal, the housing 18 can be produced by means of injection-moulding processes. Injection-moulding processes are known to constitute, on the one hand, a very convenient process and, on the other hand, a very precise process for manufacturing for example housing parts. However, only through the selection of an amorphous metal is it possible to produce the presently described housings 18 for stopcocks 11 for hand-held medical instruments.

LIST OF REFERENCE SIGNS

10 Endoscope
11 Stopcock
12 Shaft part
13 Main body
14 Inlet connector
15 Eyepiece
16 Grip piece
17 Grip piece
18 Housing
19 Plug
20 Cone part
21 Connection part
22 Connection part
23 Grip
24 Grip part
25 Upper section
26 Lower section
27 Spring element
28 Wall
29 Recess
30 Longitudinal axis
31 Latching means
32 Inner side

The invention claimed is:

1. A housing of a stopcock for producing and breaking a fluidic connection between at least two connection parts, the housing having at least two spring elements, and having an interior space in which a plug of the stopcock can be mounted in a rotatable manner, wherein:

the at least two spring elements are provided for form-fitting fixing of a position of the plug in the interior space of the housing, wherein the housing and at least one spring element is manufactured integrally from one part;

the at least two spring elements are formed from a housing wall of the housing;

the at least two spring elements are formed parallel to a longitudinal axis of the housing as an extension of the housing wall and forms a spring load perpendicular to the longitudinal axis;

a wedge-shaped recess is formed between each of the at least two spring elements in the housing wall; and openings of the wedge-shaped recesses are oriented towards a bottom side of the housing.

2. The housing of the stopcock according to claim 1, comprising three or more spring elements.

3. The housing of the stopcock according to claim 1, wherein the housing is produced from an amorphous metal.

4. The housing of the stopcock according to claim 1, wherein the at least two spring elements are configured to move perpendicularly or transversely to the longitudinal axis of the housing.

5. The housing of the stopcock according to claim 1, wherein a thickness of the at least two spring elements are larger than or smaller than, a wall thickness of the housing wall.

6. The housing of the stopcock according to claim 1, wherein the at least two spring elements are formed in a tab-shaped manner from the housing wall.

7. The housing of the stopcock according to claim 1, wherein three or more tab-shaped, oppositely situated spring elements are formed from the housing wall.

8. The housing of the stopcock according to claim 1, wherein the at least two spring elements include at least one latching means which serves for form-fitting fixing of the plug.

9. The housing of the stopcock according to claim 1, wherein the interior space is of conical form, wherein the housing wall converges towards a bottom side of the housing, and wherein the at least at least two spring elements follow the conical shape in this case or is formed in a cylindrical manner around the longitudinal axis, wherein the housing wall transitions into the cylindrical shape from the conical shape towards the bottom side of the housing.

10. The stopcock for producing and breaking a fluidic connection between at least two connection parts having the housing according to claim 1.

11. A method for producing the housing according to claim 1, wherein the housing and at least two spring elements are produced in one part.

12. A method for producing the housing according to claim 9, wherein the housing and the at least two spring elements are injection-moulded in one part from an amorphous metal.

* * * * *